US010188266B2

(12) United States Patent
Hashimoto et al.

(10) Patent No.: US 10,188,266 B2
(45) Date of Patent: Jan. 29, 2019

(54) ENDOSCOPIC IMAGING DEVICE FOR REDUCING DATA AMOUNT OF IMAGE SIGNAL

(71) Applicant: OLYMPUS CORPORATION, Tokyo (JP)

(72) Inventors: Hidenori Hashimoto, Sagamihara (JP); Wataru Ono, Hachioji (JP)

(73) Assignee: OLYMPUS CORPORATION, Tokyo (JP)

( * ) Notice: Subject to any disclaimer, the term of this patent is extended or adjusted under 35 U.S.C. 154(b) by 0 days.

(21) Appl. No.: 14/944,782

(22) Filed: Nov. 18, 2015

(65) Prior Publication Data

US 2016/0066769 A1 Mar. 10, 2016

Related U.S. Application Data

(63) Continuation of application No. PCT/JP2014/061858, filed on Apr. 28, 2014.

(30) Foreign Application Priority Data

May 20, 2013 (JP) .................. 2013-106329

(51) Int. Cl.
*A61B 1/045* (2006.01)
*A61B 1/00* (2006.01)
(Continued)

(52) U.S. Cl.
CPC ...... *A61B 1/00009* (2013.01); *A61B 1/00006* (2013.01); *A61B 1/00059* (2013.01);
(Continued)

(58) Field of Classification Search
CPC ... A61B 1/00009; A61B 1/00059; A61B 1/06; A61B 1/00006; A61B 1/05; A61B 1/07;
(Continued)

(56) References Cited

U.S. PATENT DOCUMENTS 5,379,757 A * 1/1995 Hiyama ................. H04N 7/18
348/76
5,408,263 A * 4/1995 Kikuchi ............. A61B 1/00059
348/223.1
(Continued)

FOREIGN PATENT DOCUMENTS

JP H10-105695 A 4/1998
JP H11-047085 A 2/1999
(Continued)

OTHER PUBLICATIONS

Introduction to CMOS Image Sensors, Jul. 24, 2002, http://web.archive.org/web/20020803193943/http://www.micro.magnet.fsu.edu/primer/digitalimaging/cmosimagesensors.html; See attached 892.*
(Continued)

*Primary Examiner* — John P Leubecker
*Assistant Examiner* — Genja Frankert
(74) *Attorney, Agent, or Firm* — Scully, Scott, Murphy & Presser, P.C.

(57) ABSTRACT

An imaging device includes: an imaging element that generates an image signal of a subject; an observation method determining unit that determines, based on identification information indicating types of a control device connected to the imaging device, whether the control device adopts a first observation method for processing an image signal indicating a plurality of images of the subject per one frame period or a second observation method for processing an image signal indicating a single image of the subject per one frame period; and a data reducing unit. If the control device adopts the second observation method, the data reducing unit reduces a data amount of the image signal to be transmitted to the control device per unit time such that a transmission rate indicating the data amount of the image signal per unit
(Continued)

time is acceptable to the control device that adopts the second observation method.

9 Claims, 15 Drawing Sheets

(51) Int. Cl.
*A61B 1/05* (2006.01)
*A61B 1/06* (2006.01)
*A61B 1/07* (2006.01)
*H04N 5/232* (2006.01)
*H04N 5/225* (2006.01)

(52) U.S. Cl.
CPC .............. *A61B 1/05* (2013.01); *A61B 1/06* (2013.01); *A61B 1/0638* (2013.01); *A61B 1/07* (2013.01); *H04N 5/23203* (2013.01); *H04N 2005/2255* (2013.01); *H04N 2209/044* (2013.01)

(58) Field of Classification Search
CPC ............ A61B 1/0638; H04N 5/23203; H04N 2209/044; H04N 2005/2255
See application file for complete search history.

(56) References Cited

U.S. PATENT DOCUMENTS

| | | | |
|---|---|---|---|
| 5,408,265 A * | 4/1995 | Sasaki | A61B 1/042 348/443 |
| 8,249,368 B2 | 8/2012 | Honda | |
| 2004/0196374 A1* | 10/2004 | Billerbeck | H04N 1/00127 348/207.1 |
| 2013/0096380 A1* | 4/2013 | Matsuzawa | A61B 1/00013 600/109 |

FOREIGN PATENT DOCUMENTS

| | | |
|---|---|---|
| JP | 2005-034166 A | 2/2005 |
| JP | 2006-288753 A | 10/2006 |
| JP | 2007-312810 A | 12/2007 |
| JP | 2008-142421 A | 6/2008 |

OTHER PUBLICATIONS

International Search Report dated Aug. 5, 2014 issued in PCT/JP2014/061858.
Japanese Office Action dated Jun. 2, 2015 issued in JP 2015-518175.
Extended Supplementary European Search Report dated Mar. 7, 2017 in European Patent Application No. 14 80 1784.1.

* cited by examiner

FIG.9
(a)
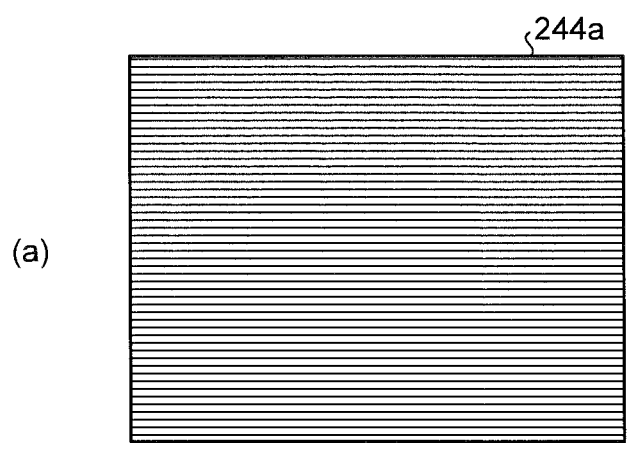
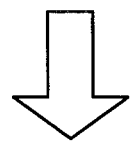
(b)
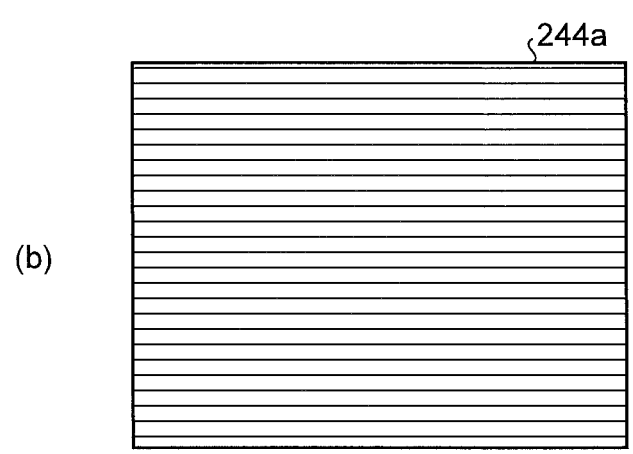

ENDOSCOPIC IMAGING DEVICE FOR REDUCING DATA AMOUNT OF IMAGE SIGNAL

CROSS-REFERENCE TO RELATED APPLICATIONS

This application is a continuation of PCT international application Ser. No. PCT/JP2014/061858 filed on Apr. 28, 2014 which designates the United States, incorporated herein by reference, and which claims the benefit of priority from Japanese Patent Application No. 2013-106329, filed on May 20, 2013, incorporated herein by reference.

BACKGROUND

1. Technical Field

The disclosure relates to an imaging device having an imaging element that can output, as image information, a photoelectrically-converted electric signal from a pixel optionally specified as a reading target among a plurality of pixels for imaging.

2. Related Art

In a medical field, an endoscope system is used at the time of observing an organ of a subject such as a patient in the related art. The endoscope system includes: an inserting unit having flexibility and an elongated shape and configured to be inserted into a body cavity of the subject; an imaging unit disposed at a distal end of the inserting unit and configured to capture an in-vivo image; and a display unit that capable of displaying the in-vivo image captured by the imaging unit. When the in-vivo image is acquired by using the endoscope system, the inserting unit is inserted into the body cavity of the subject, and then illumination light such as while light is emitted from the distal end of the inserting unit to illuminate body tissue inside the body cavity, and the imaging unit captures the in-vivo image. A user such as a doctor observes an organ of the subject based on the in-vivo image displayed on the display unit.

To perform observation by using the endoscope system, there may be a case where illumination is switched at predetermined timing among plural types of illumination. There is a known method of such an illumination method, which is a sequential lighting method in which the illumination light is sequentially switched among three color components, for example, red (R), green (G), and blue (B) (refer to Japanese Laid-open Patent Publication No. 2006-288753). According to this technology, images are individually captured under the sequentially-switched illumination light by using a charge coupled device (CCD) image sensor as an imaging element.

Further, there is a known technology of a simultaneous lighting method in which a color filter is provided on a front surface of a light receiving unit of an imaging element and imaging is performed under white illumination light.

SUMMARY

In some embodiments, an imaging device configured to be connected to a control device to perform communication includes: an imaging element configured to irradiate a subject with illumination light, capture an optical image reflected from the subject, and generate an image signal indicating a plurality of images of the subject per one frame period, the control device being configured to perform predetermined image processing on the image signal; an observation method determining unit configured to determine, based on identification information indicating types of the control device transmitted from the control device connected to the imaging device, whether the control device adopts a first observation method for processing an image signal indicating a plurality of images of the subject per one frame period or a second observation method for processing an image signal indicating a single image of the subject per one frame period; and a data reducing unit, wherein if the observation method determining unit determines that the control device connected to the imaging device adopts the second observation method, the data reducing unit is configured to reduce a data amount of the image signal to be transmitted to the control device per unit time such that a transmission rate indicating the data amount of the image signal to be transmitted to the control device per unit time is acceptable to the control device that adopts the second observation method, and is configured to transmit the image signal to the control device.

The above and other features, advantages and technical and industrial significance of this invention will be better understood by reading the following detailed description of presently preferred embodiments of the invention, when considered in connection with the accompanying drawings.

BRIEF DESCRIPTION OF THE DRAWINGS

FIG. 9 is a diagram schematically illustrating a reading area to read an image signal from a sensor unit by switching the transmission method to a different transmission method according to the first embodiment of the present invention;

DETAILED DESCRIPTION

A medical endoscope system that captures and displays an image inside a body cavity of a subject such as a patient will be described below as modes for carrying out the present invention (hereinafter referred to as "embodiment(s)"). The present invention is not limited by the embodiments. The same reference signs are used to designate the same elements throughout the drawings. Since the drawings are schematically illustrated, a relation between thicknesses and widths of respective members, ratios of the respective members, etc. may differ from an actual state. Also, there may be portions where dimensions and ratios may differ from one another among the drawings.

First Embodiment

Figure 1:
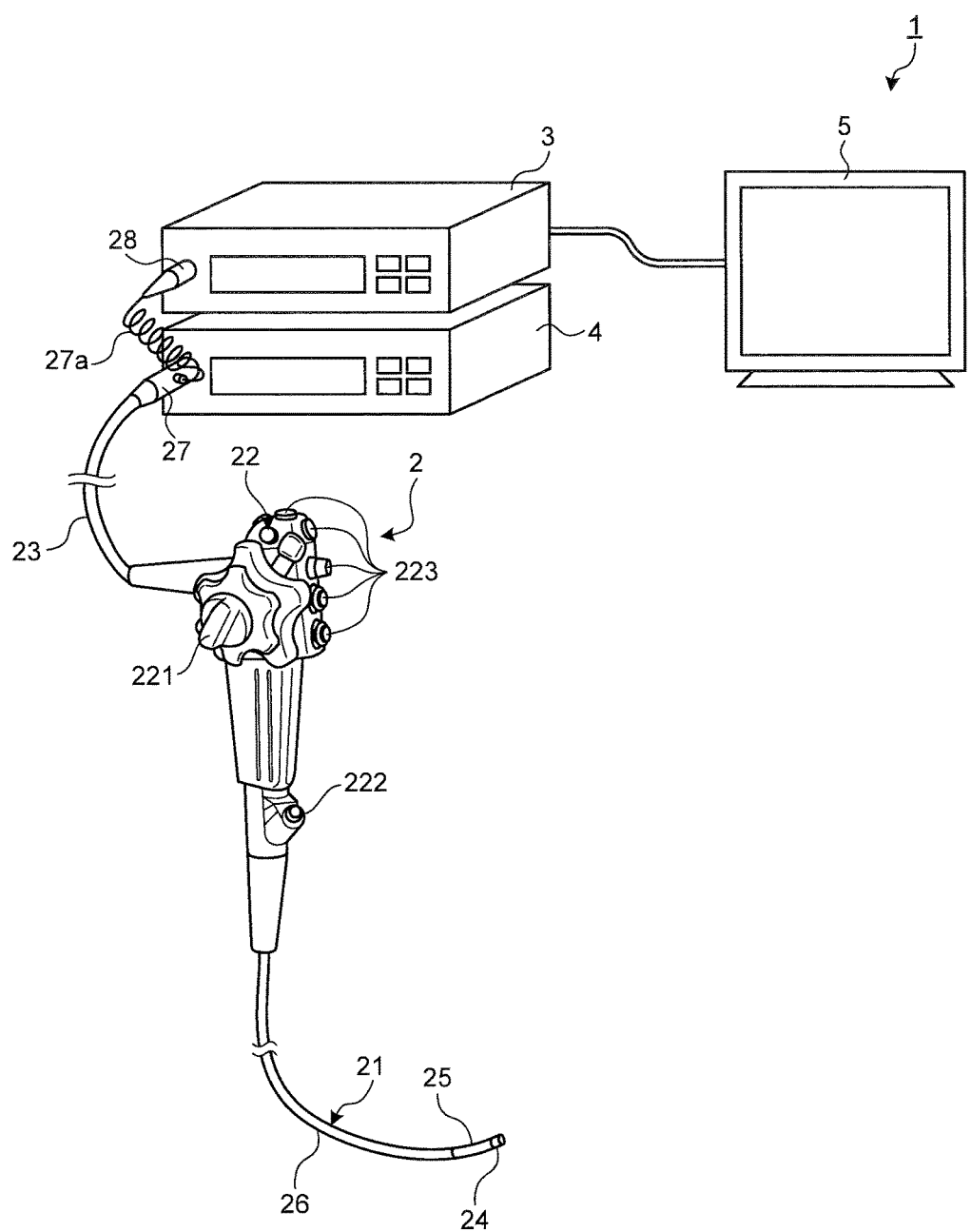
FIG. 1 is a diagram illustrating a schematic structure of an endoscope system that is an imaging device according to a first embodiment of the present invention.

FIG. 1 is a diagram illustrating a schematic structure of an endoscope system that is an imaging device according to a first embodiment of the present invention. As illustrated in FIG. 1, an endoscope system 1 includes an endoscope 2 that captures an in-vivo image of a subject by inserting a distal end portion into a body cavity of the subject, a control device 3 that performs predetermined image processing on the in-vivo image captured by the endoscope 2 and further integrally controls operation of the entire endoscope system 1, a light source device 4 that generates illumination light to emit light from a distal end of the endoscope 2, and a display device 5 that displays the in-vivo image subjected to the image processing by the control device 3.

The endoscope 2 includes an inserting unit 21 having flexibility and an elongated shape, an operating unit 22 that is connected to a proximal end side of the inserting unit 21 and receives various kinds of operation signals, and a universal cord 23 that extends in a direction different from an extending direction of the inserting unit 21 from the operating unit 22 and includes various kinds of cables connecting the control device 3 to the light source device 4.

The inserting unit 21 includes a distal end portion 24 incorporating an imaging element described later, a curved portion 25 that is formed of a plurality of curved pieces and can be freely curved, and a long-shaped flexible tube portion 26 that is connected to a proximal end side of the curved portion 25 and has flexibility.

Figure 2:
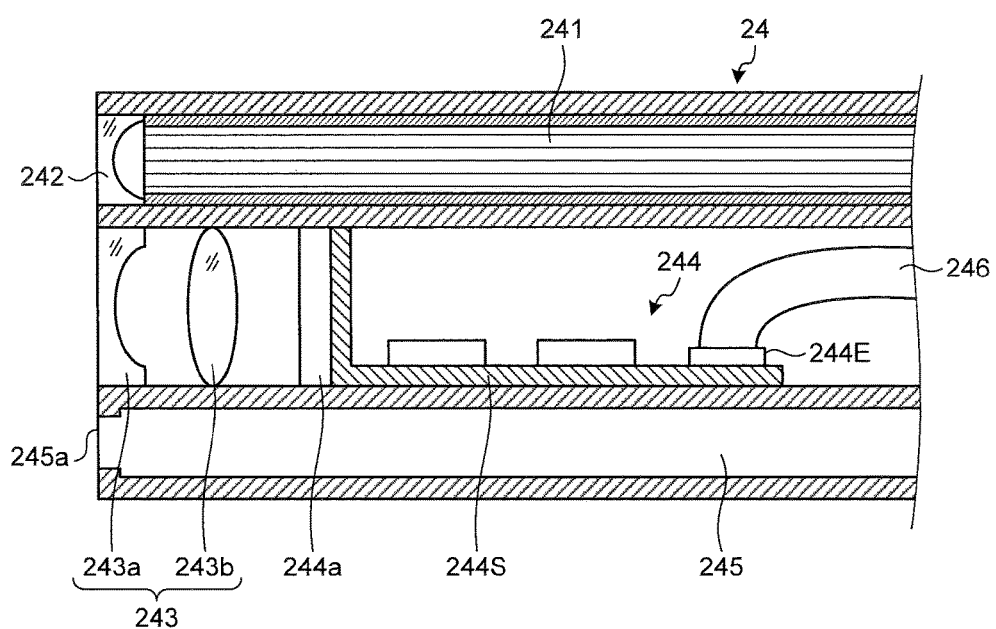
FIG. 2 is a cross-sectional view for describing an outline of an internal structure of a distal end portion of an endoscope in FIG. 1.

FIG. 2 is a cross-sectional view for describing an outline of an internal structure of the distal end portion 24. As illustrated in FIG. 2, the distal end portion 24 includes: a light guide 241 that is formed by using a glass fibers or the like and constitutes a light guide path for light generated by the light source device 4; an illumination lens 242 provided at a distal end of the light guide 241; an optical system 243 for light condensing; an imaging element 244 that is provided at an image forming position of the optical system 243 and receives light condensed by the optical system 243 and photoelectrically converts the light to an electric signal, and then performs predetermined signal processing on the electric signal; and a treatment tool channel 245 through which a treatment tool for the endoscope 2 is configured to pass.

The optical system 243 is formed of at least a lens 243$a$ and a lens 243$b$. Note that kinds and the number of lenses constituting the optical system 243 are not limited to those illustrated in FIG. 2.

Figure 3:
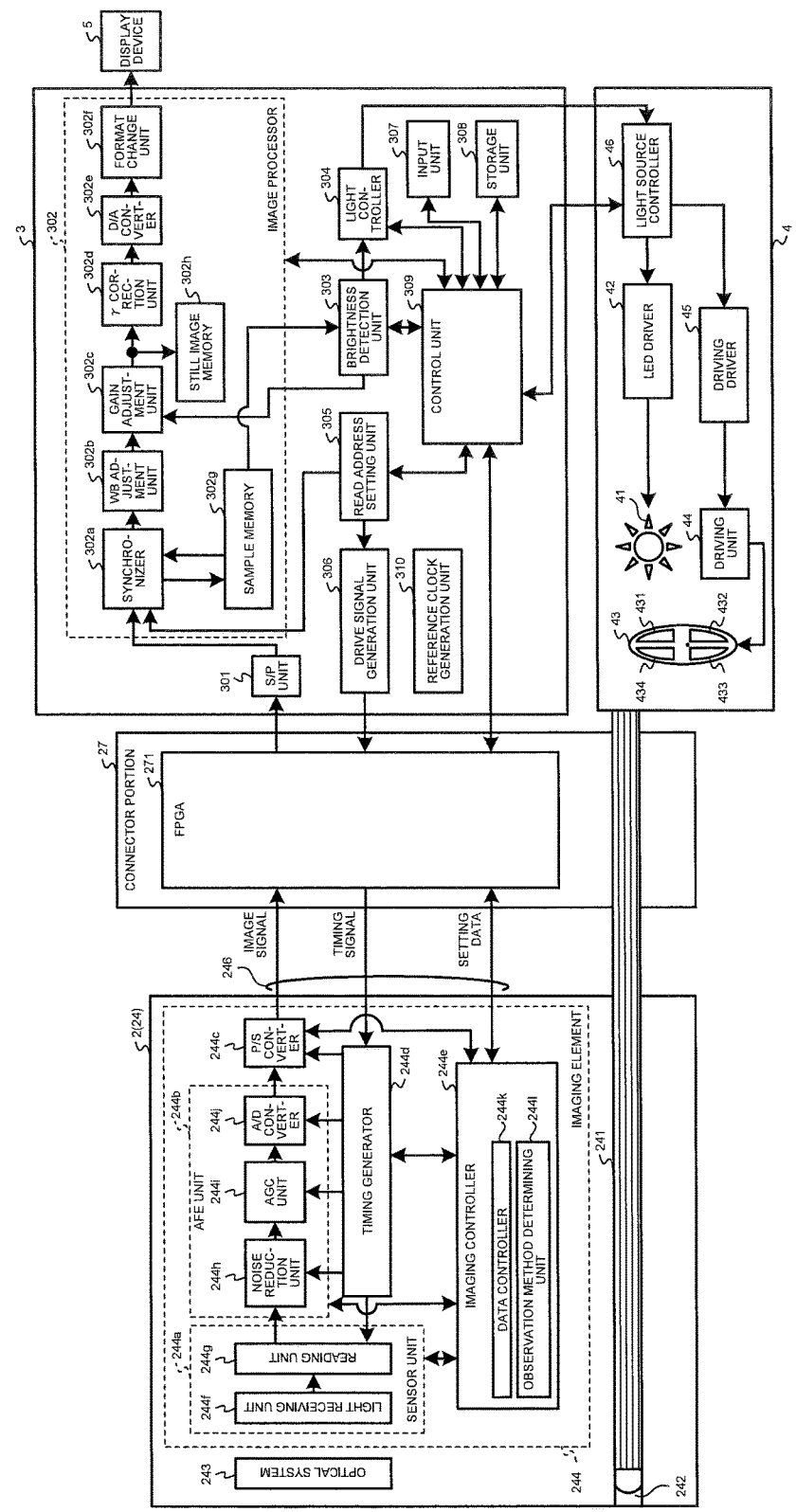
FIG. 3 is a block diagram illustrating a functional configuration of a main portion of the endoscope system according to the first embodiment of the present invention.

FIG. 3 is a block diagram illustrating a functional configuration of a main portion of the endoscope system 1. A configuration of the imaging element 244 will be described with reference to FIG. 3. As illustrated in FIG. 3, the imaging element 244 includes a sensor unit 244$a$ that outputs an electric signal by photoelectrically converting an optical image received from the optical system 243, an analog front end 244$b$ (hereinafter, referred to as "AFE unit 244$b$") that performs noise removal and A/D conversion on the electric signal output from the sensor unit 244$a$, a P/S converter 244$c$ that performs parallel-serial conversion on a digital signal output from the AFE unit 244$b$, a timing generator 244$d$ that generates driving timing of the sensor unit 244$a$ and pulses for various kinds of signal processing performed in the AFE unit 244$b$ and P/S converter 244$c$, and an imaging controller 244$e$ that controls operation of the imaging element 244. The imaging element 244 is a complementary metal oxide semiconductor (CMOS) image sensor.

The sensor unit 244$a$ includes: a light receiving unit 244$f$ in which a plurality of pixels each having a photodiode that accumulates electric charge in accordance with a light amount, and further each having an amplifier that amplifies the electric charge accumulated by the photodiode are arranged in two-dimensional matrix form; and a reading unit 244$g$ that reads, as image information, an electric signal generated by a pixel optionally set as a reading target from among the plurality of pixels in the light receiving unit 244$f$.

The AFE unit 244$b$ includes a noise reduction unit 244$h$ that reduces noise components included in an electric signal (analog), an auto gain control (AGC) unit 244$i$ that maintains a constant output level by adjusting an amplification factor (gain) of the electric signal, and an A/D converter 244$j$ that performs A/D conversion on the electric signal output via the AGC unit 244$i$. The noise reduction unit 244$h$ performs noise reduction by using, for example, a correlated double sampling method.

The imaging controller 244$e$ controls various kind of operation of the distal end portion 24 according to setting data received from the control device 3. The imaging controller 244$e$ is formed by using a central processing unit (CPU) and the like. The imaging controller 244$e$ includes a data controller 244$k$ and an observation method determining unit 244$l$.

The data controller 244$k$ controls a data amount of an image signal to be transmitted to the control device 3 based on setting data received from the control device 3. More specifically, the data controller 244$k$ sets an area to be read by the reading unit 244$g$ based on the setting data received from the control device 3. Here, the setting data includes identification information of the control device 3 and observation information indicating an observation method such as a sequential lighting method and a simultaneous lighting method, an imaging speed (frame rate) of the imaging element 244, a command information providing a command of a reading speed for pixel information from an optional pixel of the sensor unit 244$a$, transmission control information for the pixel information read by the AFE unit 244$b$, and so on. For example, the data controller 244k reduces the data amount of an image signal output from the sensor unit 244a by reducing a reading area based on a determination result by the observation method determining unit 244l described later, compared to adopting the sequential lighting method. In the reading area, the reading unit 244g reads out the image information from the light receiving unit 244f. In other words, the reading unit 244g functions as a data reducing unit according to the first embodiment.

The observation method determining unit 244l determines, based on the identification information of the control device 3 included in the setting data received from the control device 3, whether the control device 3 adopts the simultaneous lighting method in which an image signal of the subject is generated by capturing an image of the subject irradiated with white light. Note that the observation method determining unit 244l may determine another observation method, such as the sequential lighting method, based on the setting data received from the control device 3.

An electrode 244E provided on a substrate 244S is connected to a cable assembly 246 in which a plurality of signal lines through which an electric signal is exchanged with the control device 3 are bundled. The plurality of signal lines includes a signal line that transmits the image signal output from the imaging element 244 to the control device 3, a signal line that transmits a control signal output from the control device 3 to the imaging element 244, and so on.

The operating unit 22 includes a curving knob 221 that curves the curved portion 25 in vertical and horizontal directions, a treatment tool inserting unit 222 from which a treatment tool such as a biological forceps, a laser knife, or a test probe is inserted into a body cavity, and a plurality of switches 223 functioning as an operation input unit to receive an operation command signal of peripheral devices such as an air feeding unit, a water feeding unit, and a gas feeding unit in addition to the control device 3 and the light source device 4. The treatment tool inserted from the treatment tool inserting unit 222 is exposed from an opening 245a via the treatment tool channel 245 of the distal end portion 24.

The universal cord 23 includes at least the light guide 241 and the cable assembly 246. The universal cord 23 includes a connector portion 27 detachably attached to the light source device 4 (refer to FIG. 1). The connector portion 27 has a coil-like coil cable 27a extending therefrom, and includes an electric connector portion 28 detachably attached to the control device 3 at an extending end of the coil cable 27a. The connector portion 27 includes a field programmable gate array (FPGA) 271 inside thereof.

Next, a configuration of the control device 3 will be described. The control device 3 includes an S/P converter 301, an image processor 302, a brightness detection unit 303, a light controller 304, a read address setting unit 305, a drive signal generation unit 306, an input unit 307, a storage unit 308, a control unit 309, and a reference clock generation unit 310. In the first embodiment, the configuration of the control device 3 employing the sequential lighting will be described, but the simultaneous lighting method can be also used.

The S/P converter 301 performs serial-parallel conversion on the image signal (digital signal) received from the distal end portion 24.

The image processor 302 generates an in-vivo image to be displayed on the display device 5 based on the image signal in a parallel form output from the S/P converter 301. The image processor 302 includes a synchronizer 302a, a white balance (WB) adjustment unit 302b, a gain adjustment unit 302c, a $\gamma$ correction unit 302d, a D/A converter 302e, a format change unit 302f, a sample memory 302g, and a still image memory 302h.

The synchronizer 302a inputs the image signal received as pixel information in three memories (not illustrated) provided per pixel, sequentially updates values of the respective memories while retaining these values associated with addresses of pixels of the light receiving unit 244f having been read by the reading unit 244g, and further synchronizes the image signals of the three memories as an RGB image signal. The synchronizer 302a sequentially outputs the synchronized RGB image signals to the white balance adjustment unit 302b, and outputs a part of the RGB image signal to the sample memory 302g for image analysis such as brightness detection.

The white balance adjustment unit 302b automatically adjusts white balance of the RGB image signal. More specifically, the white balance adjustment unit 302b automatically adjusts the white balance of the RGB image signal based on a color temperature included in the RGB image signal.

The gain adjustment unit 302c adjusts a gain of the RGB image signal. The gain adjustment unit 302c outputs the RGB signal subjected to the gain adjustment to the $\gamma$ correction unit 302d and further outputs, to the still image memory 302h, a part of the RGB signal for displaying a still image, displaying an enlarged image, or displaying an emphasized image.

The $\gamma$ correction unit 302d performs gradation correction ($\gamma$ correction) of the RGB image signal to conform to the display device 5.

The D/A converter 302e converts, to an analog signal, the RGB image signal output from the $\gamma$ correction unit 302d and subjected to the gradation correction.

The format change unit 302f changes the image signal converted to the analog signal in a moving image file format such as a high vision format, and outputs the same to the display device 5.

The brightness detection unit 303 detects a brightness level corresponding to each pixel from the RGB image signal retained by the sample memory 302g, and records the detected brightness level in a memory provided inside thereof, and then outputs the brightness level to the control unit 309. In addition, the brightness detection unit 303 calculates a gain adjustment value and a light irradiation amount based on the detected brightness level, and outputs the gain adjustment value to the gain adjustment unit 302c while outputting the light irradiation amount to the light controller 304.

Under the control of the control unit 309, the light controller 304 sets a type, a light amount, emitting timing, etc. of the light generated by the light source device 4 based on the light irradiation amount calculated by the brightness detection unit 303, and transmits a light source synchronization signal including these setting conditions to the light source device 4.

The read address setting unit 305 has a function to set pixels to be read and a reading order on a light receiving surface of the sensor unit 244a. In other words, the read address setting unit 305 has a function to set addresses of the pixels of the sensor unit 244a to be read by the AFE unit 244b. Further, the read address setting unit 305 outputs, to the synchronizer 302a, address information of the pixels set as reading targets.

The drive signal generation unit 306 generates a drive timing signal for driving the imaging element 244, and transmits the timing signal to the timing generator 244d via a predetermined signal line included in the cable assembly 246. The timing signal includes the address information of the pixels to be read.

The input unit 307 receives various kinds of signals such as an operation command signal that provides a command to operate the endoscope system 1.

The storage unit 308 is implemented by using semiconductor memory such as flash memory and dynamic random access memory (DRAM). The storage unit 308 stores various kinds of programs for operating the endoscope system 1 and data including various kinds of parameters and the like required to operate the endoscope system 1. Further, the storage unit 308 stores the identification information of the control unit 309 and the observation information. Here, the identification information includes unique information (ID) of the control unit 309, a model year, specification information and transmission rate information of the control unit 309.

The control unit 309 is formed by using, for example, a CPU and performs drive control of respective components including the distal end portion 24 and the light source device 4, and also controls input/output of information relative to the respective components. The control unit 309 transmits, to the imaging controller 244e, setting data for imaging control via a predetermined signal line included in the cable assembly 246.

The reference clock generation unit 310 generates a reference clock signal to be a reference of operation in each of the components of the endoscope system 1, and supplies the generated reference clock signal to each of the components of the endoscope system 1.

Next, a configuration of the light source device 4 will be described. The light source device 4 includes a light source 41, a light emitting diode (LED) driver 42, a rotary filter 43, a driving unit 44, a driving driver 45, and a light source controller 46.

The light source 41 is formed by using a white LED or a xenon lamp, for example, and generates white light under the control of the light source controller 46. The LED driver 42 supplies current to the light source 41 under the control of the light source controller 46, thereby causing the light source 41 to generate white light. The light generated by the light source 41 is emitted from the distal end of the distal end portion 24, passing through the rotary filter 43, a condenser lens (not illustrated), and the light guide 241.

The rotary filter 43 is disposed and rotated on an optical path of the white light generated by the light source 41, thereby transmitting only light having a predetermined wavelength band out of the white light generated by the light source 41. More specifically, the rotary filter 43 includes a red filter 431, a green filter 432, a blue filter 433, and a transparent filter 434 which are configured to transmit light having respective wavelength bands of red light (R), green light (G), blue light (B), and white light. Rotational movement of the rotary filter 43 sequentially transmits the light having the wavelength bands of red, green, blue, and white (for example, red: 600 nm to 700 nm, green: 500 nm to 600 nm, blue: 400 nm to 500 nm, white: 400 nm to 700 nm). Thus, the white light generated by the light source 41 can sequentially emit any one of narrow-band red light, green light, blue light, and white light to the endoscope 2.

The driving unit 44 is formed by using, for example, a step motor and a DC motor, and rotates and operates the rotary filter 43. The driving driver 45 supplies predetermined current to the driving unit 44 under the control of the light source controller 46.

The light source controller 46 controls a current amount to be supplied to the light source 41 in accordance with the light source synchronization signal transmitted from the light controller 304. Further, the light source controller 46 rotates the rotary filter 43 by driving the driving unit 44 via the driving driver 45 under the control of the control unit 309.

The display device 5 has functions to receive the in-vivo image generated by the control device 3 from the control device 3 via a video cable and display the in-vivo image. The display device 5 is formed by using a liquid crystal display or an organic electro luminescence (EL).

Figure 4:
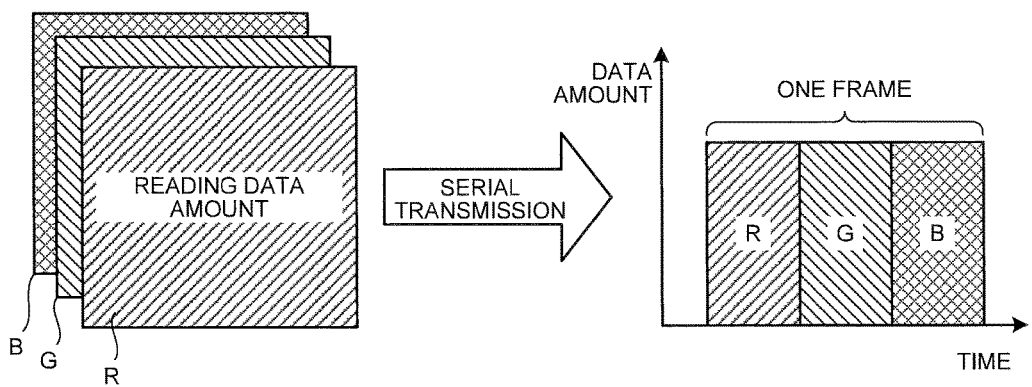
FIG. 4 is a diagram schematically illustrating an outline of an image capturing method of a sequential lighting method executed by the endoscope of the endoscope system according to the first embodiment of the present invention.
Figure 5:
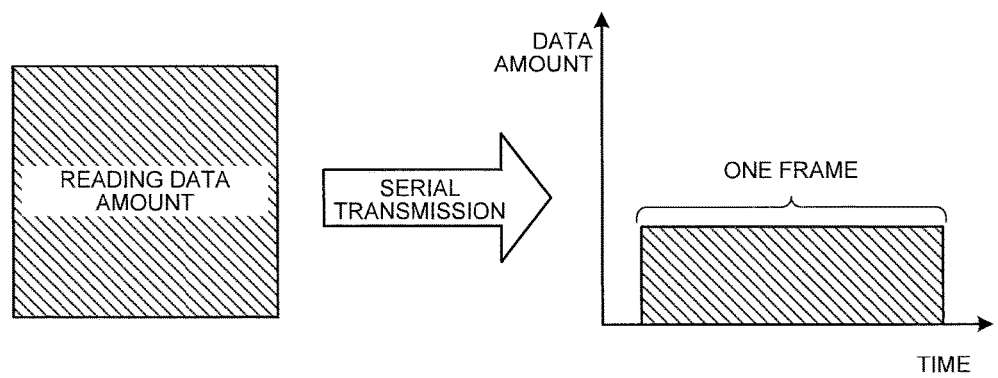
FIG. 5 is a diagram schematically illustrating an outline of an image capturing method executed by the endoscope of a simultaneous lighting method.

An image capturing method executed by the endoscope system 1 having the above-described configuration will be described. FIG. 4 is a diagram schematically illustrating an outline of the image capturing method of the sequential lighting method executed by the endoscope 2 of the endoscope system 1 according to the first embodiment. FIG. 5 is a diagram schematically illustrating an outline of the image capturing method executed by the endoscope 2 of the simultaneous lighting method.

As illustrated in FIG. 4, the endoscope 2 of the endoscope system 1 adopts the sequential lighting method in which illumination light having different wavelengths is emitted at the predetermined timing as described above, and reflection light is sequentially imaged synchronizing with the illumination light. For this reason, as illustrated in FIG. 4, in the case of outputting one frame of an image signal of a biological image, the number of reading times from the sensor unit 244a is to be three times (red, green, blue are respectively imaged) while the number of reading times is once in the simultaneous lighting method (refer to FIG. 5). Accordingly, the endoscope 2 has larger transmission data amount transmitted to the control device 3 (about three times), compared to the simultaneous lighting method. As a result, in the case of transmitting the image signal to the control device 3 in the endoscope 2 of the endoscope system 1 according to the first embodiment, when the control device 3 can be only applied to the simultaneous lighting method, processing capacity of the control device 3 and resolution of the image signal are degraded because the data amount and transmission rate of the image signal to be transmitted are different.

Therefore, the endoscope 2 inside the endoscope system 1 according to the first embodiment switches a reading area to read the image information from the sensor unit 244a based on the identification information and the observation information included in the setting data received by the data controller 244k from the control device 3, thereby reducing the data amount of the image signal to be transmitted to the control device 3.

Figure 6:
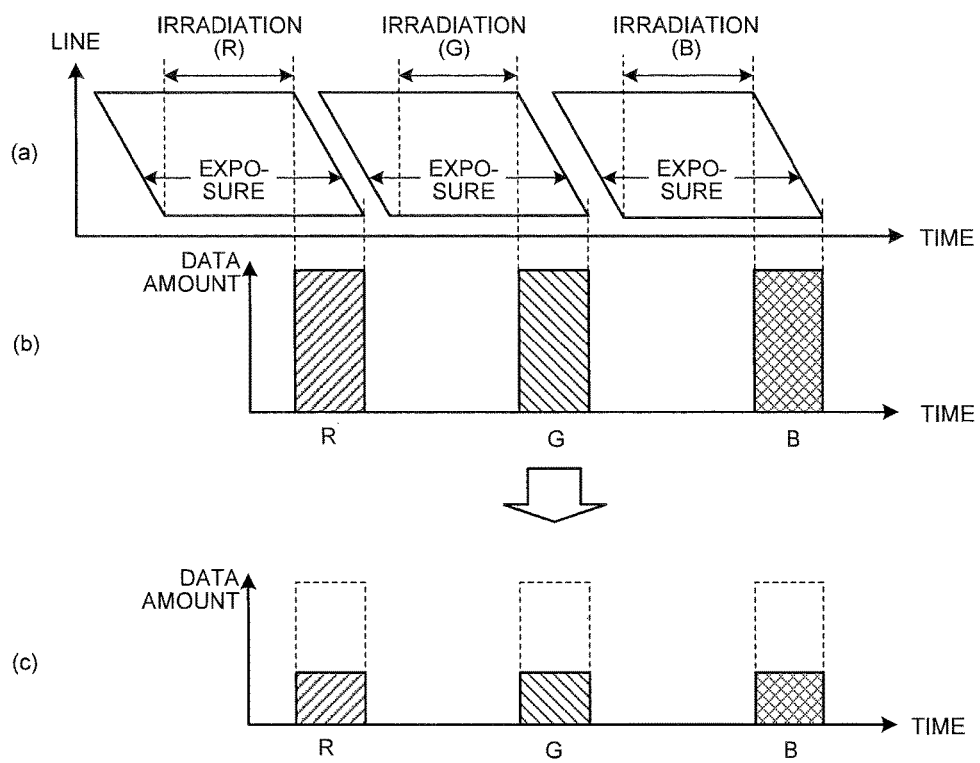
FIG. 6 is a diagram schematically illustrating a relation between the outline of the image capturing method that can be executed by the endoscope system according to the first embodiment of the present invention and a data amount of an image signal to be transmitted to a control device.

FIG. 6 is a diagram schematically illustrating a relation between the outline of the image capturing method that can be executed by the endoscope system 1 according to the first embodiment and the data amount of the image signal to be transmitted to the control device 3. The imaging element 244 is the CMOS image sensor as described above, and a focal plane electronic shutter (rolling shutter) is adopted. Therefore, in the case of consecutively imaging a plurality of frames, the imaging element 244 sequentially reads accumulated electric charge per horizontal line. As a result, there is a time difference between a horizontal line first read and a horizontal line finally read by the imaging element 244. Further, in FIG. 6, FIG. 6(a) illustrates a relation between imaging timing of the imaging element 244 and illumination light, FIG. 6(b) illustrates a data amount when an image signal is transmitted to the control device 3 that can be applied to the sequential lighting method, and FIG. 6(c) illustrates a data amount when an image signal is transmitted to the control device 3 that can be applied to the simultaneous lighting method. Note that a vertical axis represents the horizontal lines (lines) of the imaging element 244 and a horizontal axis represents time in FIG. 6(a). Further, in FIGS. 6(b) and 6(c), a vertical axis represents a transmitting data amount of the image signal and a horizontal axis represents time.

Figure 7:
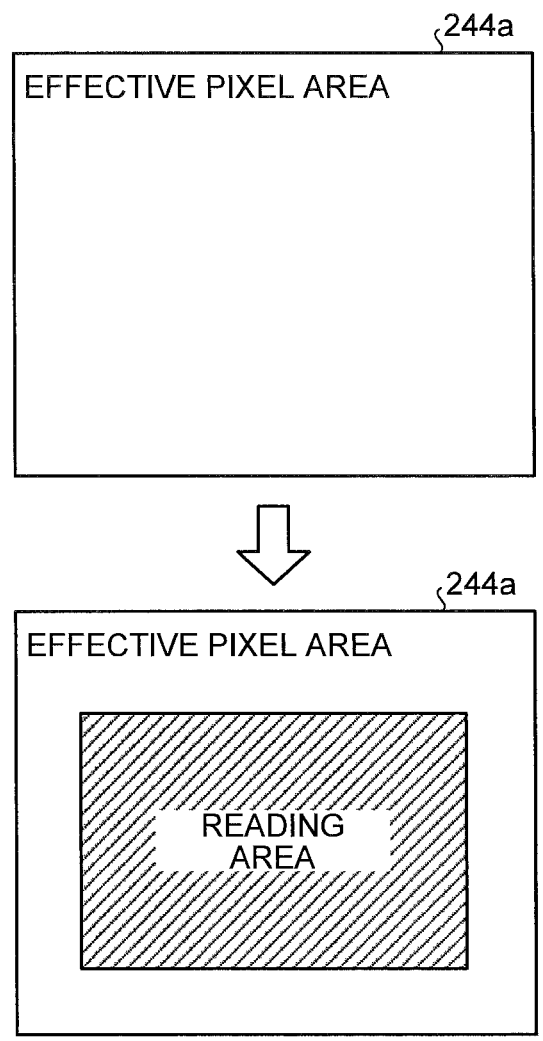
FIG. 7 is a diagram schematically illustrating a reading area to read an image signal from a sensor unit by switching a transmission method according to the first embodiment of the present invention.

In the case illustrated in FIG. 6(a), the light source device 4 sequentially emits the illumination light, for example, red→green→blue, in respective predetermined timing. At this point, the imaging element 244 sequentially reads pixels, starting from a horizontal line at an upper portion of a screen to lower-side horizontal lines immediately after the light source device 4 finishes emitting the illumination light. Therefore, as illustrated in FIG. 6(b), the data amount of the data to be transmitted by the imaging element 244 of the endoscope 2 is increased. Accordingly, as illustrated in FIG. 7, if the control device 3 adopts the simultaneous lighting method, the data controller 244k makes the sensor unit 244a perform imaging by switching a reading area such that the reading area where the reading unit 244g reads the image information from the sensor unit 244a becomes smaller than the reading area of the control device 3 that can be applied to the sequential lighting method. Thus, as illustrated in FIG. 6(c), the endoscope 2 reduces the data amount of the image information to be transmitted to the control device 3, thereby standardizing the transmission rate and the control device 3 regardless of an applicable type of the observation method in the control device 3.

Figure 8:
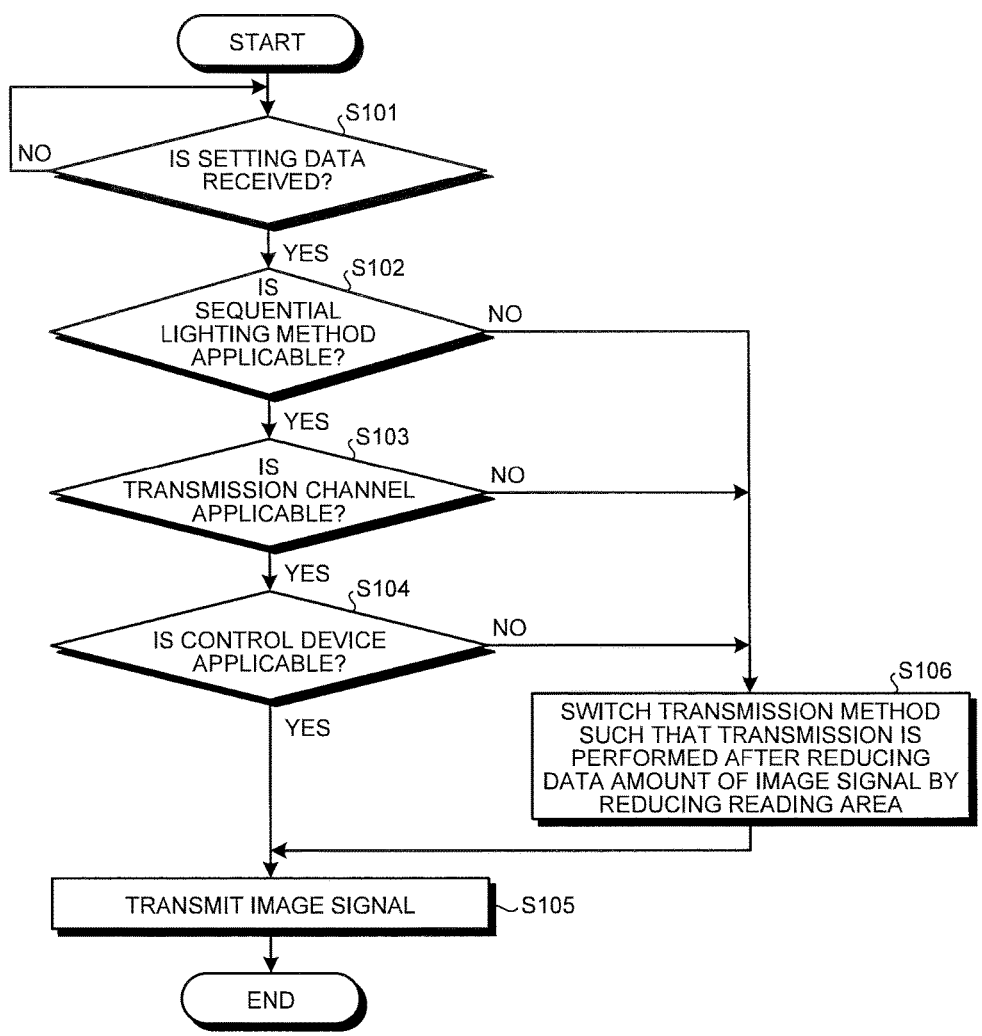
FIG. 8 is a flowchart illustrating an outline of processing executed by the endoscope system according to the first embodiment of the present invention.

Next, processing executed by the endoscope system 1 according to the first embodiment will be described. FIG. 8 is a flowchart illustrating an outline of the processing executed by the endoscope system 1 according to the first embodiment. The following processing is performed at a predetermined timing: at the time of performing initial operation after power is supplied to the endoscope system 1 immediately after the endoscope 2 is connected to the control device 3; before an operator starts examining a subject by using the endoscope system 1; or between the examinations of the subject.

As illustrated in FIG. 8, the imaging controller 244e determines whether the setting data is received from the control device 3 (Step S101). In the case of receiving the setting data from the control device 3 (Step S101: Yes), the imaging controller 244e proceeds to Step S102. On the other hand, if the setting data is not received from the control device 3 (Step S101: No), the imaging controller 244e continues the same determination.

Subsequently, if the observation method determining unit 244l determines that the control device 3 can be applied to the observation method of the sequential lighting method based on the setting data received from the control device 3 (Step S102: Yes) and further determines that a transmission channel (transmission rate) to transmit an image signal can be applied (Step S103: Yes) and when that the control device 3 can be applied (Step S104: Yes), the data controller 244k transmits the image signal generated by the sensor unit 244a (Step S105) and finishes this processing.

In contrast, if the observation method determining unit 244l determines that the control device 3 cannot be applied to the observation method of the sequential lighting method based on the setting data received from the control device 3 (Step S102: No), and the transmission channel to transmit the image signal cannot be applied (Step S103: No), and the control device 3 cannot be applied (Step S104: No), the data controller 244k switches the transmission method such that transmission is performed after reducing a data amount of the image signal to be transmitted to the control device 3 by reducing a reading area where the reading unit 244g performs reading from the sensor unit 244a (Step S106). After that, the data controller 244k proceeds to Step S105.

According to the first embodiment described above, the sensor unit 244a is made to perform imaging while the data controller 244k reduces the reading area (image capturing area) where the reading unit 244g reads the image information from the sensor unit 244a smaller than a reading area (image capturing area) of the simultaneous lighting method based on the identification information and observation information included in the setting data received from the control device 3. Thus, the endoscope 2 can reduce the data amount of the image information to be transmitted to the control device 3. As a result, the endoscope 2 can transmit the image signal such that the transmission rate and the control device 3 can be standardized regardless of applicability of the observation method to the control device 3.

Further, according to the first embodiment, the observation method determining unit 244l determines the identification information of the control device 3 and the data controller 244k adjusts the data amount of the image signal to be transmitted. Therefore, the image signal can be transmitted such that the transmission rate is standardized even in the cases of a new-generation control device 3 and an older-generation control device 3.

In the first embodiment, the data controller 244k switches the reading area, where reading from the sensor unit 244a is performed, in accordance with the identification information and the observation information included in the setting data received from the control device 3. However, for example, the data amount of the image information can be reduced while decimating lines in the reading area to perform reading from the sensor unit 244a. More specifically, if the control device 3 is applicable to, for example, only the simultaneous lighting method based on the identification information and the observation information included the setting data received from the control device 3, the data controller 244k reduces the data amount of the image signal as illustrated in FIG. 9 such that the reading area which is read by the sensor unit 244a can be applied to the reading area of the simultaneous lighting method. More specifically, as illustrated in FIGS. 9(a) and 9(b), the data controller 244k causes the sensor unit 244a to perform imaging by decimating horizontal lines at equal intervals in the reading area where the reading unit 244g performs reading from the sensor unit 244a. Thus, the endoscope 2 can standardize the transmission channel and the control device 3 by reducing the data amount of the image information to be transmitted to the control device 3 regardless of applicability of the observation information to the control device 3 and a transmission type of the transmission channel.

Second Embodiment

Next, a second embodiment of the present invention will be described. An endoscope system according to the second embodiment has a same configuration as an embodiment described above, and processing executed by an endoscope of the endoscope system is different. Therefore, the processing executed by the endoscope system according to the second embodiment will be described below. The same reference signs are used to designate the same elements.

Figure 10:
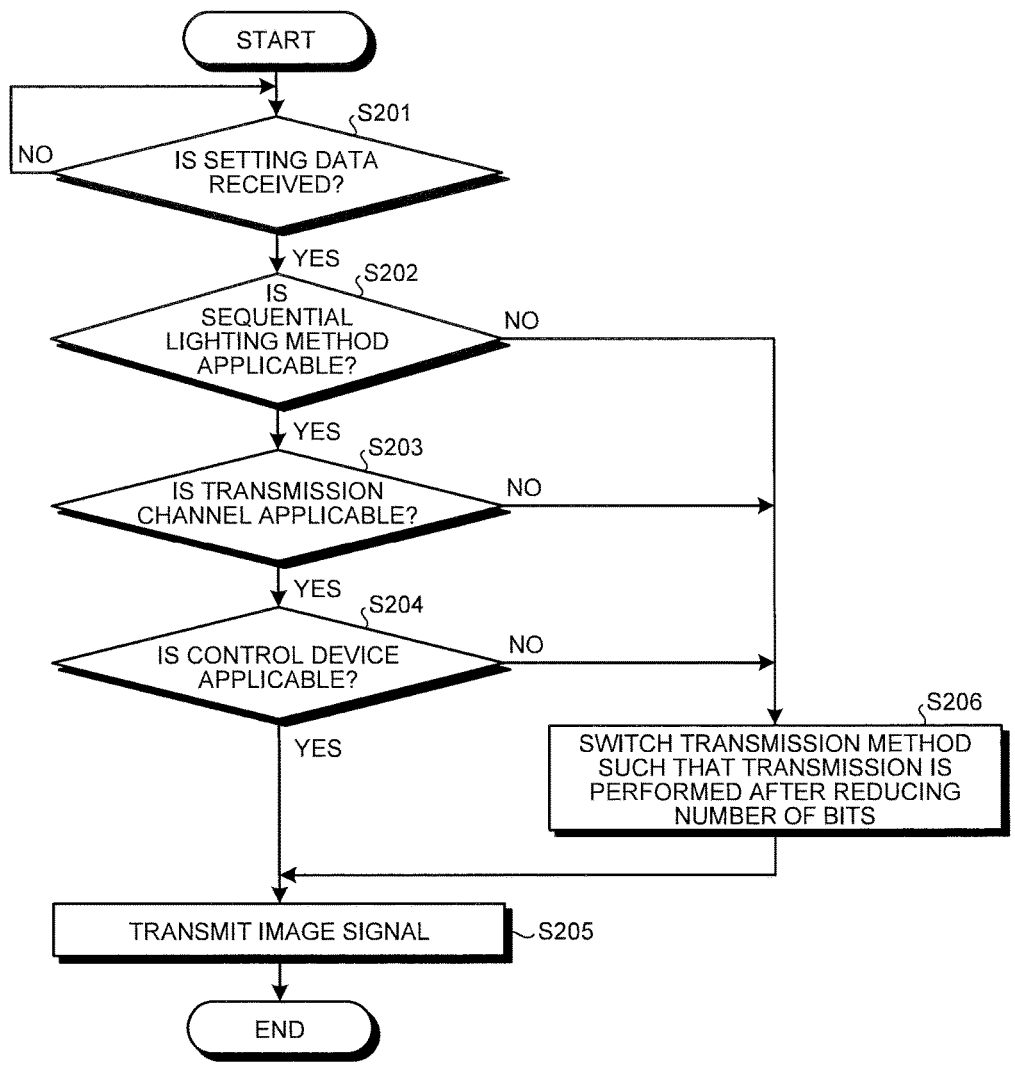
FIG. 10 is a flowchart illustrating an outline of processing executed by an endoscope system according to a second embodiment of the present invention.

FIG. 10 is a flowchart illustrating an outline of the processing executed by an endoscope system 1 according to the second embodiment.

Steps S201 to S205 correspond to Steps S101 to S105 in FIG. 8 respectively.

In Step S206, a data controller 244k switches a transmission method such that transmission to a control device 3 is performed after reducing number of bits by decimating data strings of an image signal. More specifically, if a control device 3 is applicable to, for example, only a simultaneous lighting method based on a determination result by an observation method determining unit 244l, the data controller 244k reduces the number of bits of image signal to be converted at an A/D converter 244j to the number of bits of image signal data applicable to the simultaneous lighting method. For example, the data controller 244k reduces the number of the image signal data to be converted by the A/D converter 244j from 10 bits to 8 bits. Thus, an endoscope 2 reduces the data amount of the image signal to be transmitted to the control device 3 thereby standardizing a transmission rate and the control device 3 regardless of the observation method applicable to the control device 3, the types and performance thereof. After Step S206, the endoscope system 1 proceeds to Step S205. Note that the A/D converter 244j functions as a data reducing unit in the second embodiment.

According to the second embodiment described above, the data controller 244k switches the transmission method to the transmission method in which transmission is performed after the number of bits of the image signal data is reduced by decimating the data strings of the image signal relative to the A/D converter 244j that converts an analog image signal generated by a sensor unit 244a to a digital image signal based on setting data received from the control device 3. Thus, the endoscope 2 reduces the data amount of the image signal to be transmitted to the control device 3 thereby standardizing a transmission channel and the control device 3 regardless of the observation method applicable to the control device 3, the types and performance thereof.

In the second embodiment described above, the imaging controller 244e reduces the data amount transmitting the image signal by degrading resolution of the number of bits to be converted by the A/D converter 244j. However, such data reducing may be switched such that the number of bits is decimated at an FPGA 271 disposed inside the connector portion 27 that connects the endoscope 2 to the control device 3. Thus, the data amount of the image signal can be reduced immediately before being transmitted to the control device 3 from the endoscope 2.

Third Embodiment

Next, a third embodiment of the present invention will be described. An endoscope system according to the third embodiment differs from embodiments described above in a configuration of an imaging element of an endoscope and also processing executed by the endoscope system. Therefore, in the following, the configuration of the endoscope system according to the third embodiment will be described, and then the processing executed by the endoscope system according to the third embodiment will be described. The same reference signs are used to designate the same elements.

Figure 11:
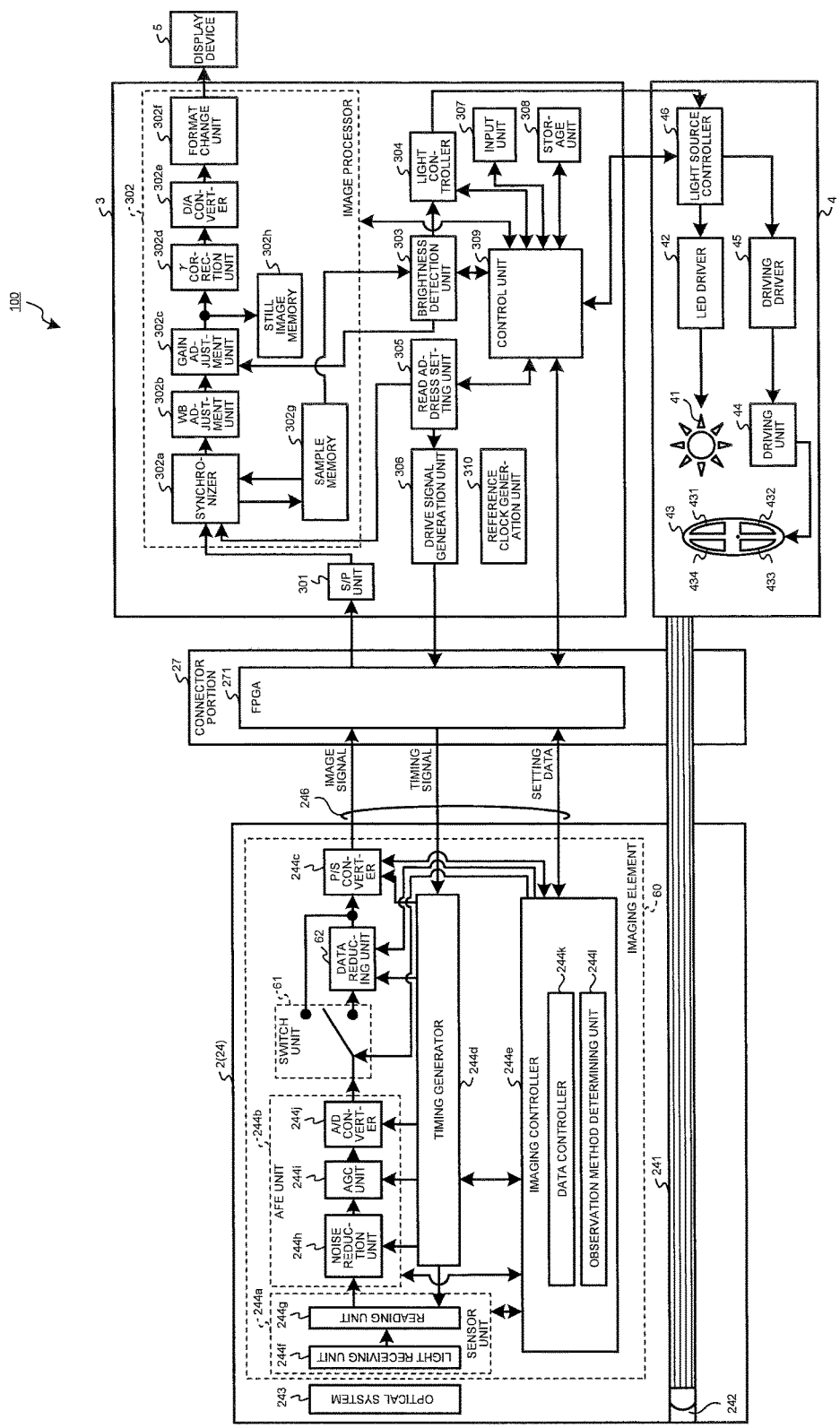
FIG. 11 is a block diagram illustrating a functional configuration of a main portion of an endoscope system according to a third embodiment of the present invention.

FIG. 11 is a block diagram illustrating a functional configuration of a main portion of an endoscope system 100 according to the third embodiment. The endoscope system 100 illustrated in FIG. 11 includes an imaging element 60 at a distal end portion 24 of an endoscope 2.

The imaging element 60 includes a sensor unit 244a, an AFE unit 244b, a P/S converter 244c, a timing generator 244d, an imaging controller 244e, a switch unit 61, and a data reducing unit 62.

The switch unit 61 is formed by using a semiconductor switch and the like. The switch unit 61 switches a transmission channel of an image signal output from the AFE unit 244b under the control of the imaging controller 244e. For example, the switch unit 61 switches the transmission channel of an image signal output from the AFE unit 244b to a transmission channel provided with the data reducing unit 62.

The data reducing unit 62 reduces a data amount transmitted at one time by leveling the data of the image signal. More specifically, the data reducing unit 62 reduces the data amount of the image signal to be transmitted by reducing the data amount of image signal data to be transmitted per unit time. The data reducing unit 62 is partly formed by using a memory.

Figure 12:
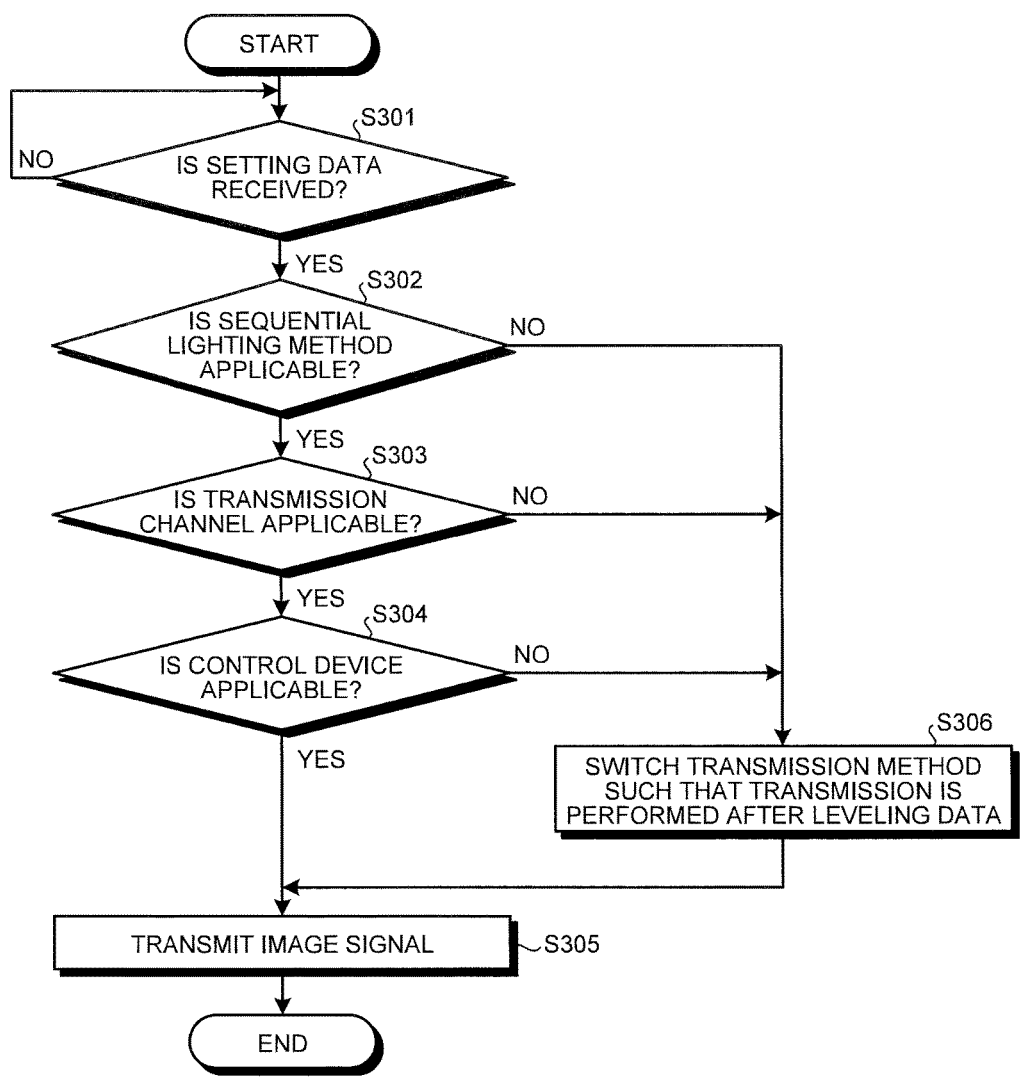
FIG. 12 is a flowchart illustrating an outline of processing executed by the endoscope system according to the third embodiment of the present invention.

The processing executed by the endoscope system 100 thus configured will be described. FIG. 12 is a flowchart illustrating an outline of the processing executed by the endoscope system 100 according to the third embodiment.

Steps S301 to S305 correspond to Steps S101 to S105 in FIG. 8 respectively.

In Step S306, the data controller 244k switches a transmission method by switching the switch unit 61 such that image signal data is transmitted after the image signal data is leveled by switching the transmission channel of the image signal output from the AFE unit 244b to the transmission channel provided with the data reducing unit 62.

Figure 13:
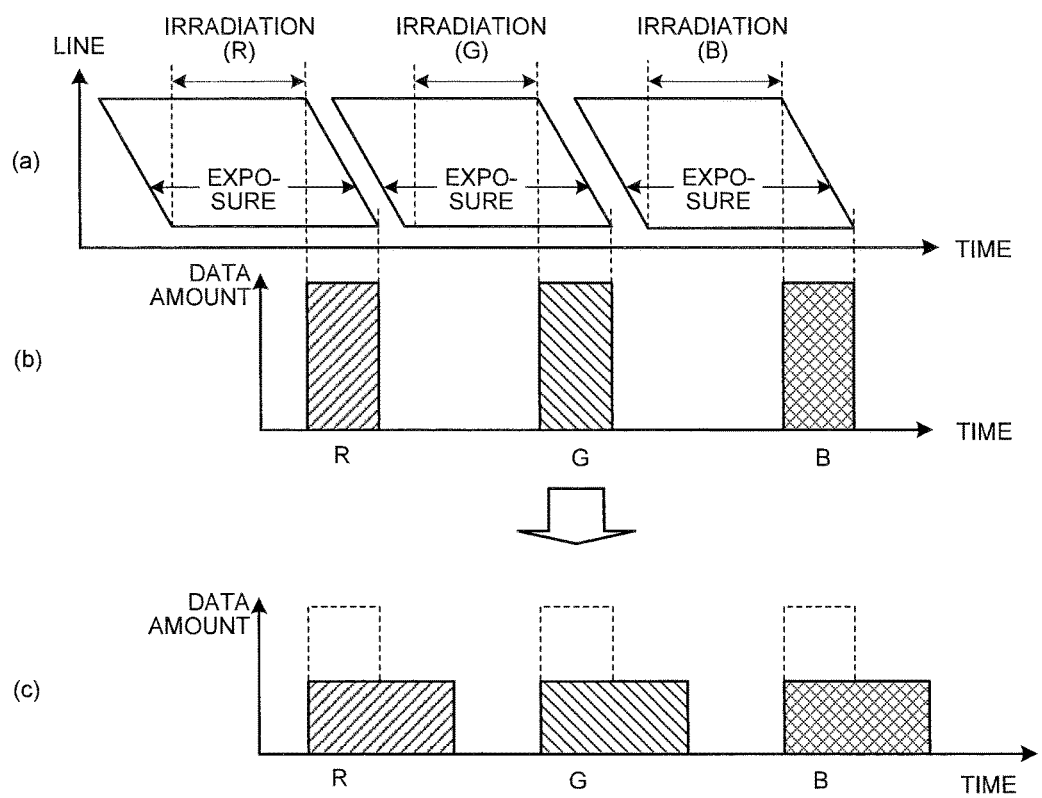
FIG. 13 is a diagram schematically illustrating a relation between an outline of an image capturing method that can be executed by the endoscope system according to the third embodiment of the present invention and a data amount of an image signal to be transmitted to a control device.

Here, the transmission method switched by the data controller 244k will be described. FIG. 13 is a diagram schematically illustrating a relation between an outline of an image capturing method that can be executed by the endoscope system 100 according to the third embodiment and a data amount of an image signal to be transmitted to a control device 3 from the endoscope 2. Further, in FIG. 13, FIG. 13(a) illustrates a relation between imaging timing of the imaging element 60 and illumination light, FIG. 13(b) illustrates a data amount when an image signal is transmitted to the control device 3 applicable to the sequential lighting method, and FIG. 13(c) illustrates a data amount when an image signal is transmitted to the control device 3 applicable to the simultaneous lighting method. Note that a vertical axis represents the horizontal lines (lines) of the imaging element 60 and a horizontal axis represents time in FIG. 13(a). Further, in FIGS. 13(b) and 13(c), a vertical axis represents a transmitting data amount of the image signal and a horizontal axis represents time.

In the case illustrated in FIG. 13(a), a light source device 4 sequentially emits the illumination light in each of predetermined timing. In this case, the imaging element 60 sequentially reads pixels, starting from a horizontal line at an upper portion of a screen to lower-side horizontal lines immediately after the light source device 4 finishes emitting the illumination light. Therefore, as illustrated in FIG. 13(b), the data amount of the image signal output by the imaging element 60 of the endoscope 2 is increased. Therefore, the imaging controller 244e switches a data transmission channel where the image signal is output via the switch unit 61 to the data reducing unit 62 side. Thus, as illustrated in FIG. 13(c), the data reducing unit 62 reduces the data amount to be output at one time to the control device 3 from the imaging element 60 by leveling the data amount of the image signal, thereby reducing a transmission rate. Further, the data reducing unit 62 can transmit the image signal to the control device 3 without losing the data amount of the image signal itself because the image signal is only needed to be output before starting reading of a next sensor unit 244*a*. After Step S306, the endoscope system 100 proceeds to Step S305.

According to the third embodiment described above, the data controller 244*k* switches the transmission channel where the sensor unit 244*a* outputs data via the switch unit 61 to the transmission channel provided with the data reducing unit 62 based on a determination result of an observation method determining unit 244*l*. Thus, the data reducing unit 62 can reduce the data amount to be transmitted to the control device 3 from the imaging element 60 at one time by leveling the data amount of the image signal output from the sensor unit 244*a*, thereby achieving to reduce the transmission rate. As a result, the endoscope 2 can standardize the transmission channel and the control device 3 regardless of applicability of observation information to the control device 3 and a transmission type of the transmission channel.

Further, according to the third embodiment, the data reducing unit 62 levels the image signal data before reading the image signal from the sensor unit 244*a* is started. Therefore, the image signal can be transmitted to the control device 3 without losing the data amount of the image signal itself.

Figure 14:
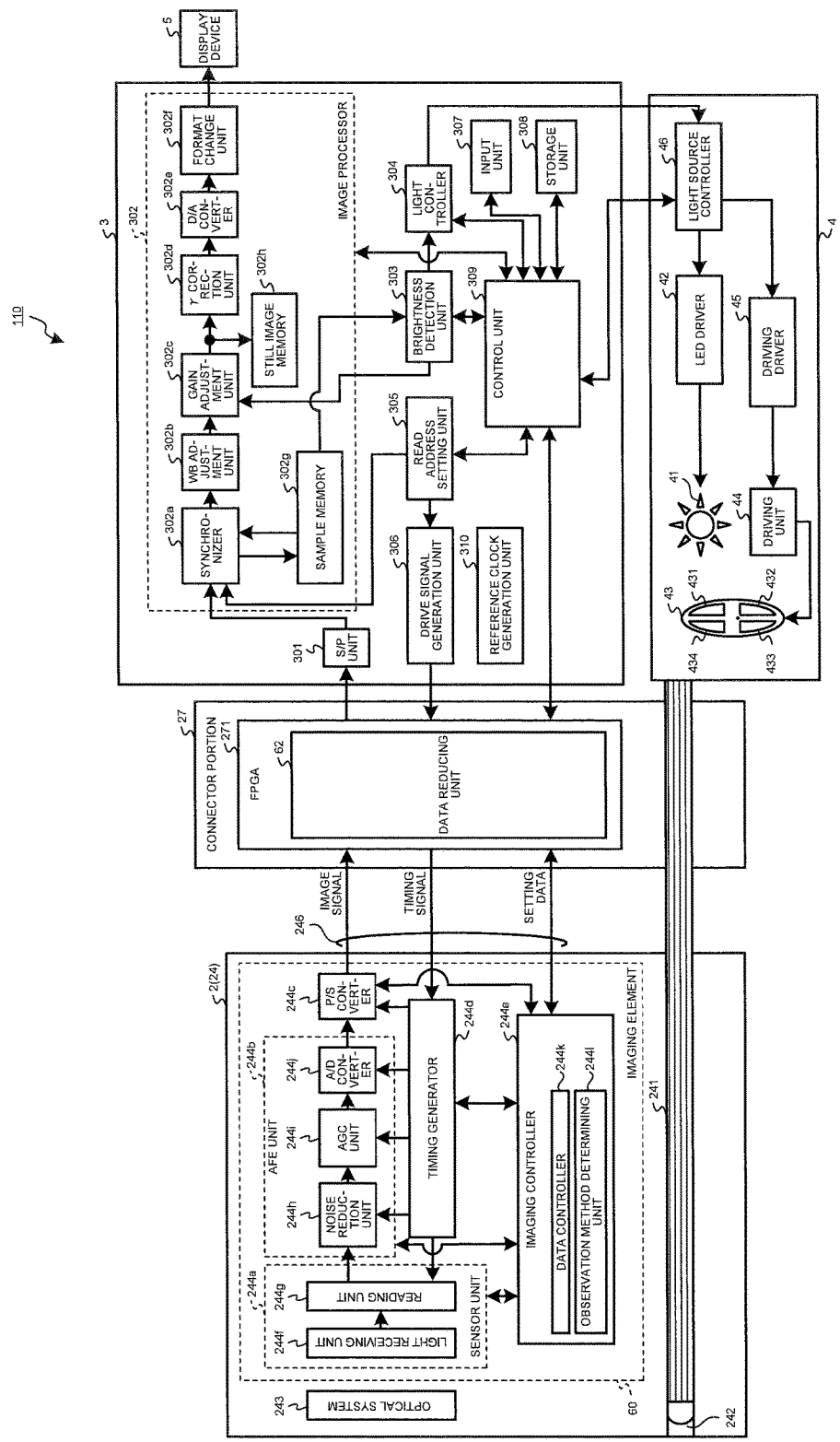
FIG. 14 is a block diagram illustrating functional configuration of a main portion of the endoscope system according to a modified example of the third embodiment of the present invention.

In the third embodiment described above, the data reducing unit 62 is provided inside the imaging element 244, but the data reducing unit 62 may be provided inside an FPGA 271 disposed inside a connector portion 27 as illustrated in FIG. 14. Thus, the data amount of the image signal can be reduced immediately before being transmitted to the control device 3 from the endoscope 2.

Fourth Embodiment

Next, a fourth embodiment of the present invention will be described. An endoscope system according to the fourth embodiment differs from above-described embodiments in a configuration of an imaging element of an endoscope and processing executed by the endoscope system. Therefore, in the following, the configuration of the endoscope system according to the fourth embodiment will be described, and then the processing executed by the endoscope system according to the fourth embodiment will be described. The same reference signs are used to designate the same elements.

Figure 15:
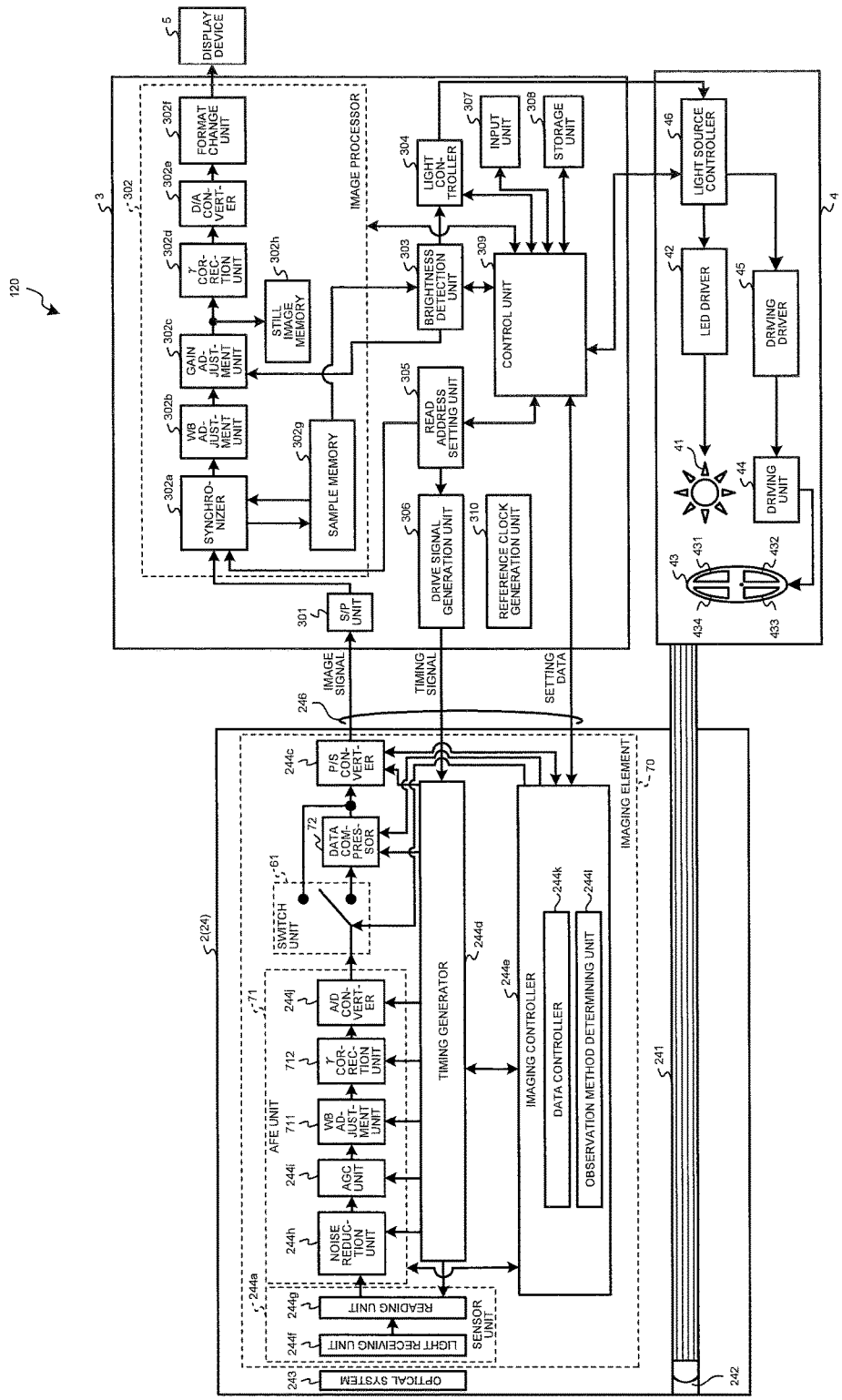
FIG. 15 is a block diagram illustrating a functional configuration of a main portion of an endoscope system according to a fourth embodiment of the present invention.

FIG. 15 is a block diagram illustrating a functional configuration of a main portion of the endoscope system according to the fourth embodiment. An endoscope system 120 illustrated in FIG. 15 includes an imaging element 70 at a distal end portion 24 of an endoscope 2.

The imaging element 70 includes a sensor unit 244*a*, a P/S converter 244*c*, a timing generator 244*d*, an imaging controller 244*e*, a switch unit 61, an AFE unit 71, and a data compressor 72.

The AFE unit 71 includes a noise reduction unit 244*h*, an AGC unit 244*i*, a WB adjustment unit 711, a γ correction unit 712, and an A/D converter 244*j*.

The WB adjustment unit 711 automatically adjusts white balance of an image signal. More specifically, the WB adjustment unit 711 automatically adjusts the white balance of the image signal based on a color temperature included in the image signal. The γ correction unit 712 performs gradation correction (γ correction) of the image signal.

The data compressor 72 reduces a data amount of an image signal by compressing the image signal received from the AFE unit 71 via the switch unit 61 in accordance with a predetermined image compression format under the control of the imaging controller 244*e*, and outputs the compressed data to the P/S converter 244*c*. Here, the predetermined format may be a joint photographic experts group (JPEG) format and the like.

Figure 16:
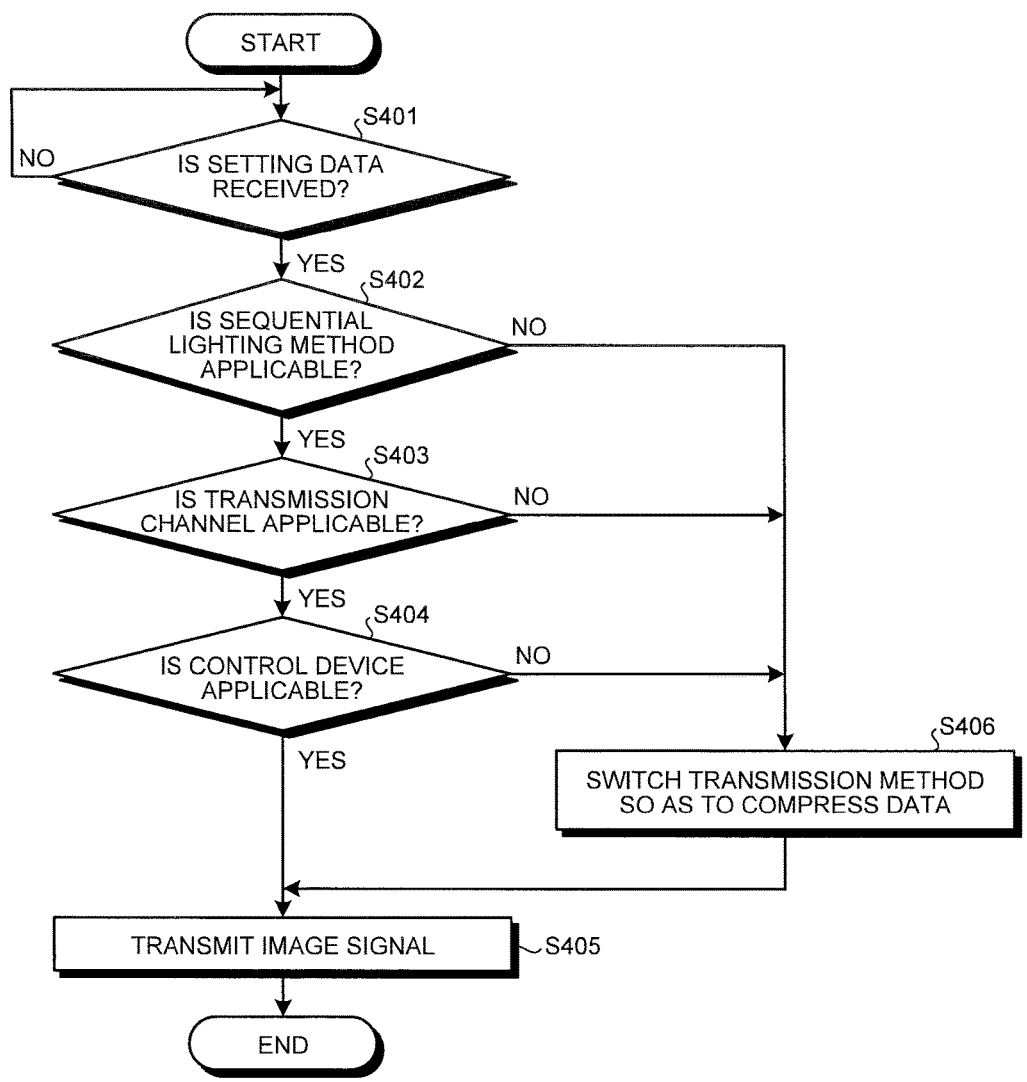
FIG. 16 is a flowchart illustrating an outline of processing executed by the endoscope system according to the fourth embodiment of the present invention.

The processing executed by the endoscope system 120 thus configured will be described. FIG. 16 is a flowchart illustrating an outline of the processing executed by the endoscope system 120 according to the fourth embodiment.

Steps S401 to S405 correspond to Steps S101 to S105 illustrated in FIG. 8 respectively.

In Step S406, the data controller 244*k* switches a transmission method by switching the switch unit 61 such that image signal data is compressed by switching a transmission channel of an image signal output from the AFE unit 71 to a transmission channel provided with the data compressor 72. More specifically, the data compressor 72 performs, on the image signal subjected to respective image processing inside the AFE unit 71, processing to compress the data, thereby reducing the image signal data to be transmitted to the control device 3. After Step S406, the endoscope system 120 proceeds to Step S405.

According to the fourth embodiment described above, the imaging controller 244*e* switches the transmission method by switching the transmission channel of the image signal to the transmission channel provided with the data compressor 72 based on a determination result of an observation method determining unit 244*l*. Thus, the data compressor 72 compresses the data amount of the image data, thereby achieving to reduce the data amount of the image signal to be transmitted to the control device 3 from the imaging element 70. As a result, the endoscope 2 can standardize the transmission rate and the control device 3 regardless of applicability of the observation method to the control device 3 and the transmission rate of the transmission channel.

Other Embodiments

In the embodiments, one imaging element is provided at a distal end portion of an endoscope, but for example, two imaging elements may be provided as well.

Further, according to the present embodiments, one light source 41 is provided at a light source device 4, but for example, a red LED, a green LED, and a blue LED may be respectively provided as well. Further, a special light source that generates exciting light emitting fluorescent marker may be provided as well.

An imaging device according to some embodiments includes a control unit configured to control a data amount of an image signal to be transmitted to a control device based on identification information of the control device connected to the imaging device. It is therefore possible to transmit the image signal regardless of types of the control device.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An imaging device comprising:
  an image sensor; and
  a processor comprising hardware, wherein the processor is configured to:
    receive information from an image processing device external to the imaging device, wherein the information indicates that the image processing device is configured to:

receive, in a transmission period defined by the image processing device, an image signal representing a single reading of a subject, illuminated by illumination light, performed by the image sensor; and generate an observation image of a first type based on the image signal representing the single reading received;

in response to the information received:

control the image sensor to perform a plurality of readings of the subject, illuminated by the illumination light;

generate an image signal representing the plurality of readings, for generating an observation image of a second type, wherein the processor is configured to control the image sensor, generate the image signal representing the plurality of readings, or both to reduce a data amount of the image signal representing the plurality of readings such that transmission of the image signal representing the plurality of readings to the image processing device is completed within the transmission period; and control a communication interface to transmit the image signal having the data amount that is reduced to the image processing device within the transmission period.

2. The imaging device according to claim 1,
wherein the processor is configured to control the image sensor to reduce an image capturing area of the image sensor to reduce the data amount of the image signal representing the plurality of readings.

3. The imaging device according to claim 1,
wherein the processor is configured to decimate a reading area for reading the image signal from an image capturing area of the image sensor to reduce the data amount of the image signal representing the plurality of readings.

4. The imaging device according to claim 3,
wherein the processor is configured to reduce number of bits by decimating data strings of the image signal to reduce the data amount of the image signal representing the plurality of readings.

5. The imaging device according to claim 3,
wherein the processor is configured to perform compression processing according to a predetermined image compression format to reduce the data amount of the image signal representing the plurality of readings.

6. The imaging device according to claim 1, further comprising:
an insertion portion configured to be inserted into the subject, wherein the image sensor is arranged at a distal end of the insertion portion;
an operating unit configured to receive input of a command signal for providing commands of various kinds of operation; and
a connector comprising the communication interface.

7. The imaging device according to claim 1, further comprising:
an insertion portion configured to be inserted into the subject, wherein the image sensor is arranged at a distal end of the insertion portion.

8. The imaging device according to claim 1,
wherein a data amount of the image signal representing the single reading of the subject performed by the image sensor is equal to or less than a predetermined data amount, and
wherein the processor is configured to reduce the data amount of the image signal representing the plurality of readings to be equal to or less than the predetermined data amount.

9. The imaging device according to claim 1,
wherein the communication interface has a transmission rate sufficient to complete transmission of the image signal representing the single reading of the subject within the transmission period, and
wherein the processor is configured to reduce the data amount of the image signal representing the plurality of readings such that transmission of the image signal representing the plurality of readings to the image processing device by the communication interface at the transmission rate is completed within the transmission period.

* * * * *